United States Patent
Goossen et al.

(10) Patent No.: US 9,875,531 B2
(45) Date of Patent: Jan. 23, 2018

(54) BONE SUPPRESSION IN X-RAY IMAGING

(71) Applicant: KONINKLIJKE PHILIPS N.V., Eindhoven (NL)

(72) Inventors: Andre Goossen, Radbruch (DE); Raoul Florent, Ville d'Avray (FR); Claire Levrier, Rueil-Malmaison (FR); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/433,392

(22) PCT Filed: Oct. 3, 2013

(86) PCT No.: PCT/IB2013/059096
§ 371 (c)(1),
(2) Date: Apr. 3, 2015

(87) PCT Pub. No.: WO2014/054018
PCT Pub. Date: Apr. 10, 2014

(65) Prior Publication Data
US 2015/0279013 A1    Oct. 1, 2015

Related U.S. Application Data

(60) Provisional application No. 61/710,101, filed on Oct. 5, 2012.

(51) Int. Cl.
*G06T 5/50* (2006.01)
*A61B 6/12* (2006.01)
(Continued)

(52) U.S. Cl.
CPC ............... *G06T 5/50* (2013.01); *A61B 6/12* (2013.01); *A61B 6/463* (2013.01); *A61B 6/487* (2013.01);
(Continued)

(58) Field of Classification Search
CPC .. G06T 5/50; G06T 7/20; G06T 5/008; G06T 2207/30048; G06T 2207/30008;
(Continued)

(56) References Cited

U.S. PATENT DOCUMENTS 8,073,221 B2    12/2011    Kukuk et al.
8,094,904 B2    1/2012    Slabaugh et al.
(Continued)

FOREIGN PATENT DOCUMENTS

WO    2006063141 A2    6/2006
WO    2011039673 A1    4/2011
WO    2011077334 A1    6/2011

OTHER PUBLICATIONS

Deng et al, "Clinical Evaluation of Dual-Energy Bone Removal in CT Angiography of the Head and Neck: Comparision With Conventional Bone-Subtraction CT Angiography", Clinical Radiology, vol. 64, No. 5, May 1, 2009, XP026086848, p. 534-541.
(Continued)

*Primary Examiner* — Amandeep Saini

(57) ABSTRACT

The present invention relates to medical image viewing in relation with navigation in X-ray imaging. In order to provide improved X-ray images, for example for cardiac procedures, allowing a facilitated perception while ensuring that increased details are visible, a medical image viewing device (10) for navigation in X-ray imaging is provided that comprises an image data providing unit (12), a processing unit (14), and a display unit (16). The image data providing unit is configured to provide an angiographic image of a region of interest of an object. The processing unit is configured to identify a suppression area for partial bone suppression within the angiographic image, and to identify and locally suppress predetermined bone structures in the angiographic image in the suppression area, and to generate
(Continued)

a partly-bone-suppressed image. Further, the display unit is configured to display the partly-bone-suppressed image.

14 Claims, 5 Drawing Sheets

(51) Int. Cl.
*G06T 5/00* (2006.01)
*G06T 7/20* (2017.01)
*A61B 6/00* (2006.01)
*A61B 90/00* (2016.01)

(52) U.S. Cl.
CPC .............. *A61B 6/504* (2013.01); *G06T 5/008* (2013.01); *G06T 7/20* (2013.01); *A61B 6/4441* (2013.01); *A61B 6/503* (2013.01); *A61B 2090/364* (2016.02); *A61B 2090/376* (2016.02); *G06T 2207/10016* (2013.01); *G06T 2207/10116* (2013.01); *G06T 2207/10121* (2013.01); *G06T 2207/30008* (2013.01); *G06T 2207/30048* (2013.01); *G06T 2207/30101* (2013.01); *G06T 2211/404* (2013.01)

(58) Field of Classification Search
CPC ..... G06T 2211/404; G06T 2207/10016; G06T 2207/10116; G06T 2207/10121; G06T 2207/30101; A61B 6/12; A61B 6/504; A61B 6/487; A61B 6/463; A61B 2090/376; A61B 2090/364; A61B 6/503; A61B 6/4441

USPC .................................................. 382/131, 132
See application file for complete search history.

(56) References Cited

U.S. PATENT DOCUMENTS

| | | |
|---|---|---|
| 8,180,148 B2 | 5/2012 | Cover |
| 2005/0100208 A1* | 5/2005 | Suzuki ................... G06T 5/007 382/157 |
| 2006/0247521 A1* | 11/2006 | McGee .................... A61B 5/06 600/434 |
| 2008/0118127 A1 | 5/2008 | Sirohey et al. |
| 2009/0087070 A1 | 4/2009 | Slabaugh |
| 2013/0259352 A1* | 10/2013 | Wang ...................... A61B 6/50 382/132 |

OTHER PUBLICATIONS

Lell et al, "Carotid Computed Tomography Angiography With Automated Bone Suppression", Investigative Radiology, vol. 44, No. 6, 2009, pp. 322-328.

Suzuki et al, Image-Processing Technique for Suppressing Ribs in Chest Radiographs by Means for Massive Training Artificial Neural Network (MTANN), IEEE Transactions on Medical Imaging, vol. 25, No. 4, 2006, p. 406-416.

Natalia Yu.I., Kompyuternaya tekhnologiya vosstanovleniya prostranstvennoy struktury koronarnykh sosudov po angiograficheskim proektsiyam (Computer technology for reconstructing spatial structure of coronary vessels from angiographic projections), Kompyuternaya optika, vol. 33, N3, 2009, pp. 281-317.

* cited by examiner

BONE SUPPRESSION IN X-RAY IMAGING

CROSS-REFERENCE TO PRIOR APPLICATIONS

This application is the U.S. National Phase application under 35 U.S.C. §371 of International Application Serial No. PCT/IB2013/059096, filed on Oct. 3, 2013, which claims the benefit of U.S. Application Ser. No. 61/710,101, filed on Oct. 5, 2012. These applications are hereby incorporated by reference herein.

FIELD OF THE INVENTION

The present invention relates to medical X-ray imaging, and relates in particular to a medical image viewing device for navigation in X-ray imaging, a medical imaging system, a method for providing improved X-ray image navigation information, as well as to a computer program element and a computer readable medium.

BACKGROUND OF THE INVENTION

X-ray imaging is used, for example, during minimal invasive interventions, such as percutaneous cardiac interventions. To support navigation of an interventional device, fluoroscopic imaging, i.e. low dose X-ray imaging is used to visualize the current situation, for example visualizing the current delivery of a stent or the like. WO 2011/039673 A1, for example, describes vascular roadmapping, where a vessel tree extracted from an angiogram is overlaid on a live fluoroscopic image. However, it has been shown that in X-ray imaging, for example during cardiac or vascular interventions or in diagnostic X-ray for soft tissue imaging, bone structures may superpose with the target anatomy and thus might prevent or complicate perception of faint or subtle structures. Further, WO 2011/077334 relates to bone suppression in X-ray radiograms and proposes for chest X-ray to detect and remove the bones from a single X-ray acquisition. However, this is not readily applicable to suppress bone structures during cardiac angiography, because the rib appearance may be very similar to the one of small injected vessels. The method could thus suppress small vessels unintentionally.

SUMMARY OF THE INVENTION

There may thus be a need to provide improved X-ray images, for example for cardiac procedures, allowing a facilitated perception while ensuring that increased details are visible.

The object of the present invention is solved by the subject-matter of the independent claims, wherein further embodiments are incorporated in the dependent claims.

It should be noted that the following described aspects of the invention apply also for the medical image viewing device for navigation in X-ray imaging, the medical imaging system, the method for provided improved X-ray navigation, the computer program element, and the computer readable medium.

According to a first aspect of the present invention, a medical image viewing device for navigation in X-ray imaging is provided that comprises an image data providing unit, a processing unit, and a display unit. The image data providing unit is configured to provide an angiographic image of a region of interest of an object. The processing unit is configured to identify a suppression area for partial bone suppression within the angiographic image. The processing unit is further configured to identify and locally suppress predetermined bone structures in the angiographic image in the suppression area, to generate a partly-bone-suppressed image. The display unit is configured to display the partly-bone-suppressed image.

By suppressing bone structures only in selected areas of an X-ray image, the X-ray image presented to the user in form of the partly-bone-suppressed image provides detailed and undisturbed information in region of interest, while also providing the bone structures outside the identified suppression areas as anatomical markers, facilitating the navigation for the radiologist or surgeon.

According to an exemplary embodiment, the image data providing unit is configured to provide a current fluoroscopy image of the region of interest. The processing unit is configured to track a device in the fluoroscopy image, to register the fluoroscopy image and the angiographic image, to transfer a position of the tracked device to the angiographic image, and to define a predefined region around the position of the device as the suppression area.

The device comprises interventional devices such as guide wires, inserted into a vascular system, and interventional devices, for example delivered via the guide wire to the position to be treated, such as balloons for dilation and stent delivery devices, detachable coils for aneurism clotting, and the like.

In an example, the identification is provided by a mouse, keyboard, trackball or the like. The identification may also be provided by eye tracking techniques.

According to an exemplary embodiment, the image data providing unit is configured to provide a sequence of angiographic images and a sequence of fluoroscopy images. The processing unit is configured to register the detected bone structures on each angiogram image, to determine to which of the angiograms the current fluoroscopy image corresponds, to estimate motion between the determined angiogram and the current fluoroscopy image, to compute an intersection between the registered bone structures and the registered suppression area, and to output a region of interest in which the bones are to be suppressed.

Thus, a continuous stream of live images, namely a sequence, representing the current situation is provided, in which sequence the bone structures are not shown in selected areas of the used angiogram sequence.

According to a second aspect, a medical imaging system is provided that comprises an X-ray image acquisition device and a medical image viewing device. The X-ray image acquisition device comprises an X-ray source and an X-ray detector. The X-ray imaging acquisition device is configured to provide X-ray images of an object. The medical image viewing device is provided according to one of the above mentioned examples.

For example, the images used for an angiographic sequence, or an X-ray image used as an angiographic image, can be provided by the X-ray image acquisition device, which can also provide a current fluoroscopy image, in which a device is tracked, as mentioned above. In another example, the current fluoroscopy image is provided from the X-ray image acquisition device and the images used for an angiographic sequence, or an X-ray image used as an angiographic image, are provided by another imaging device.

According to a third aspect, a method for providing improved X-ray image navigation information is provided that comprised the following steps:

a) providing an angiographic image of a region of interest of an object;
b) identifying a suppression area for partial bone suppression within the angiographic image;
c) identifying and locally suppressing predetermined bone structures in the angiographic image in the suppression area, wherein a partly-bone-suppressed image is generated; and
d) displaying the partly-bone-suppressed image.

According to an exemplary embodiment, step b) comprises identifying the suppression area by an input device.

According to another exemplary embodiment, step b) comprises:
b1) providing a current fluoroscopy image of the region of interest;
b2) tracking a device in the fluoroscopy image;
b3) registering the fluoroscopy image and the angiographic image; and
b4) transferring a position of the tracked device to the angiographic image and defining a predefined region around the position of the device as the suppression area.

In an example, in step b2), a device mask image is created.

According to an exemplary embodiment, in step d), the partly-bone-suppressed image is combined with image data from the current fluoroscopy image forming a partly-bone-suppressed roadmap, and the partly-bone-suppressed roadmap is displayed.

For example, data of the fluoroscopy image is transferred into the image data of the partly-bone-suppressed image (of the angiogram), such as the device shown in the fluoroscopy image being transferred into the partly bone-suppressed angiogram image. This may be referred to as inverse road-mapping.

In another example, the complete fluoroscopy image is transferred into the partly bone-suppressed angiogram image, wherein the fluoroscopy image may be adjusted in the grade of transparency for minimum distraction.

In an example, a sequence of partly-bone-suppressed images is combined with a sequence of current fluoroscopy images forming a partly-bone-suppressed roadmap sequence.

In an example, the current fluoroscopy image, or sequence, is also subject to partly bone-suppression. The thus partly bone-suppressed image may then be shown combined with the partly-bone-suppressed image (of the angiogram) or in addition as separate image.

In another example, the current fluoroscopy image is shown separately in addition to the partly-bone-suppressed image, or in addition to the partly-bone-suppressed roadmap.

According to an exemplary embodiment, in step c), a full suppression image is computed for every detected bone, wherein the suppression is only visualized in the suppression area. In another exemplary embodiment, in step c), each bone structure intersecting with the suppression area is suppressed along its complete detected length.

In an example, the bone suppression is provided with a smoothened transition, i.e. with a smooth feathering or smooth blending, for example for suppressing borders and the progression of the suppression.

According to an exemplary embodiment, bone structures outside the suppression area are maintained and kept visible as anatomical markers, facilitating navigation.

For example, the bone suppression is provided with an adjustable degree of suppression. A degree of suppression may also be provided in dependency of the distance from the suppression area's centre point.

According to an exemplary embodiment, step c) comprises the following sub-steps: c1) detecting and segmenting bone structures; and c2) estimating their contribution to the X-ray projection.

According to an exemplary embodiment, the region of interest is the heart, and the method provides navigation support in cardiac procedures.

According to an aspect, bone structures, such as ribs or other long bones, are suppressed from an X-ray exposure sequence in a controlled and local way, such that the position of an interventional device within the fluoroscopy image determines the area of suppression of the specific bone to be suppressed in the angiogram. A full suppression image for every detected bone may be computed and the suppression may be visualized only around the detected device position, e.g. in a circular fashion, feathering the borders. A region of interest around the detected device position may be checked for intersection with bones. For example, each bone that intersects with this region of interest is suppressed along its complete detected length. In another example, bone structures are manipulated in the image, for example completely deleted or at least attenuated in their appearance, in certain areas only, for example in an area of specific interest, such as the area where a device is located. Bones overlapping with the region of interest may be completely suppressed or all bones are faded out in the region of interest. Bone structures outside the particularly defined, i.e. selected area may be left untouched and are displayed to provide further orientation for navigation. The orientation facilitates the navigation in terms of better orientation in a larger scale, whereas the suppressed areas, i.e. areas where the bone structures are suppressed, show enhanced details that are no longer disturbed in terms of visual perception and mental understanding on the side of the user, since these selected or determined regions show the complete anatomical content, except the bone structures, which are suppressed.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
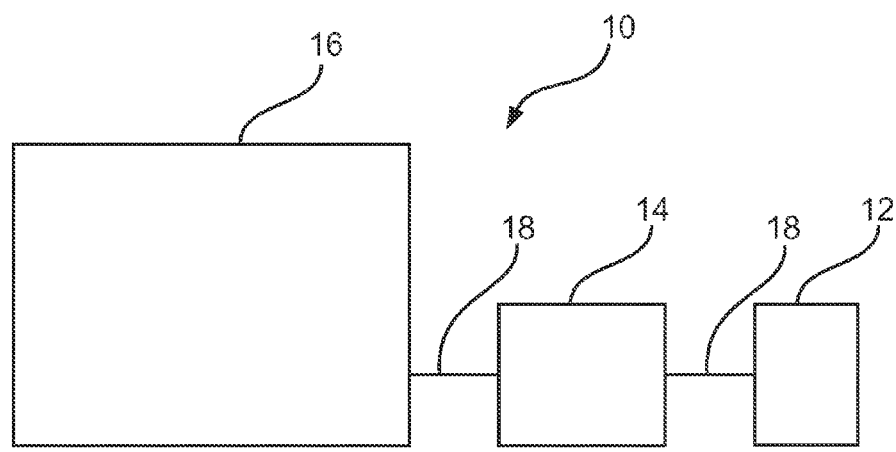
FIG. 1 shows a schematic setup of a medical image viewing device for navigation in X-ray imaging in an example.

FIG. 1 shows a medical image viewing device 10 for navigation in X-ray imaging, wherein the medical image viewing device 10 comprises an image data providing unit 12, a processing unit 14, and a display unit 16. The image data providing unit 12 is configured to provide an angiographic image of a region of interest of an object. The processing unit 14 is configured to identify a suppression area for partial bone suppression within the angiographic image, and to identify and locally suppress predetermined bone structures in the angiographic image in the suppression area, to generate a partly-bone-suppressed image. The display unit 16 is configured to display the partly-bone-suppressed image. Connecting lines 18 indicate data connection between the image data providing unit 12, the processing unit 14, and the display unit 16. The data connection can be provided by wire connection and by wireless connection.

The term "suppression area" relates to a selected portion of the image, in which portion suppression is applied, concerning bone structures.

In an example, not further shown, the image data providing unit 12 is configured to provide a current fluoroscopy image of the region of interest. The processing unit is configured to track a device in the fluoroscopy image, to register the fluoroscopy image and the angiographic image, to transfer a position of the tracked device to the angiographic image and to define a predefined region around the position of the device as the suppression area.

According to a further example (not further shown), the image data providing unit 12 is configured to provide a sequence of angiographic images and a sequence of fluoroscopy images. The processing unit is configured to register the detected bone structures on each angiogram image, to determine to which of the angiograms the current fluoroscopy image corresponds, to estimate motion between the determined angiogram and the current fluoroscopy image, and to compute an intersection between the registered bone structures and the registered suppression area, and to output a region of interest in which the bones are to be suppressed.

Figure 2:
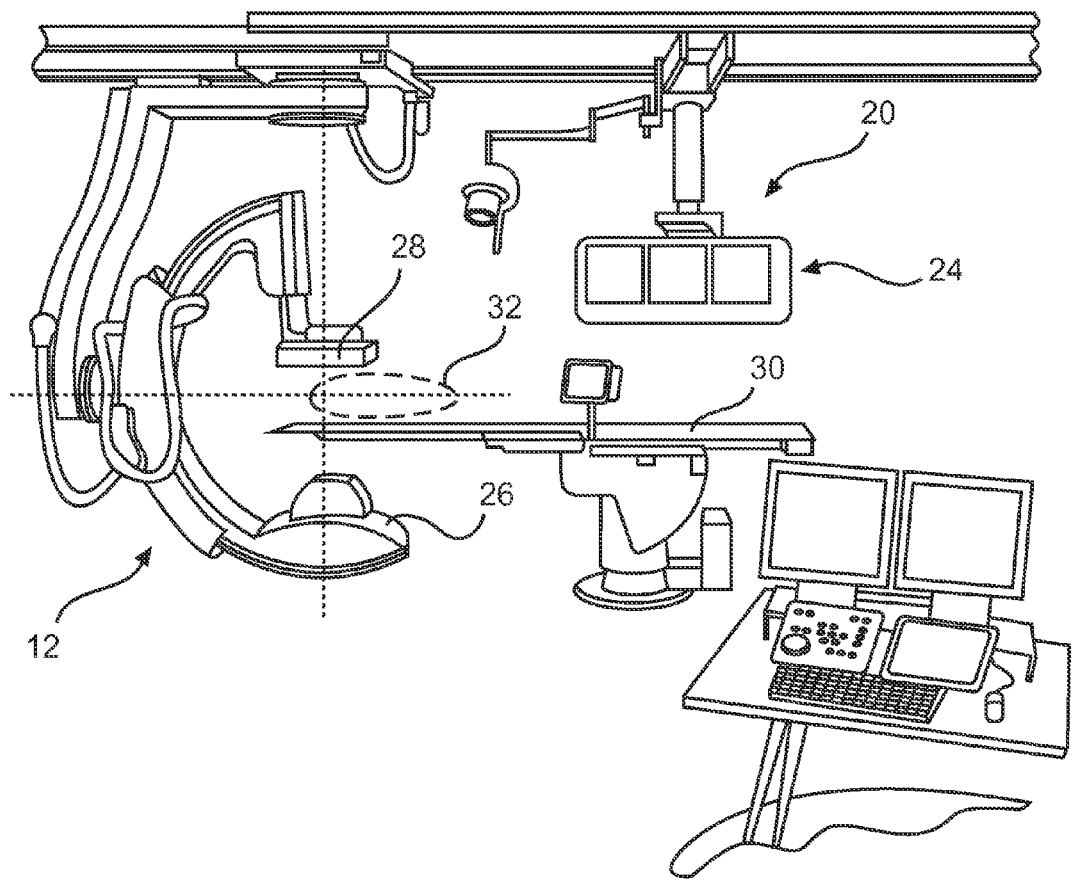
FIG. 2 shows a medical imaging system.

According to the example of FIG. 2, a medical imaging system 20 is provided, comprising an X-ray image acquisition device 22, and a medical image viewing device 24. The X-ray image acquisition device comprises an X-ray source 26 and an X-ray detector 28. The X-ray image acquisition device 22 is configured to provide X-ray images of an object. The medical image viewing device 24 is provided as a medical image viewing device according to one of the above mentioned examples. Further, a support table 30, for example for receiving an object 32, such as a patient, is shown in FIG. 2.

It should be noted that the X-ray image acquisition device 22 shown in FIG. 2 is shown as a C-arm structure. However, also other X-ray image acquisition devices, movable or non-movable, are provided.

Figure 3:
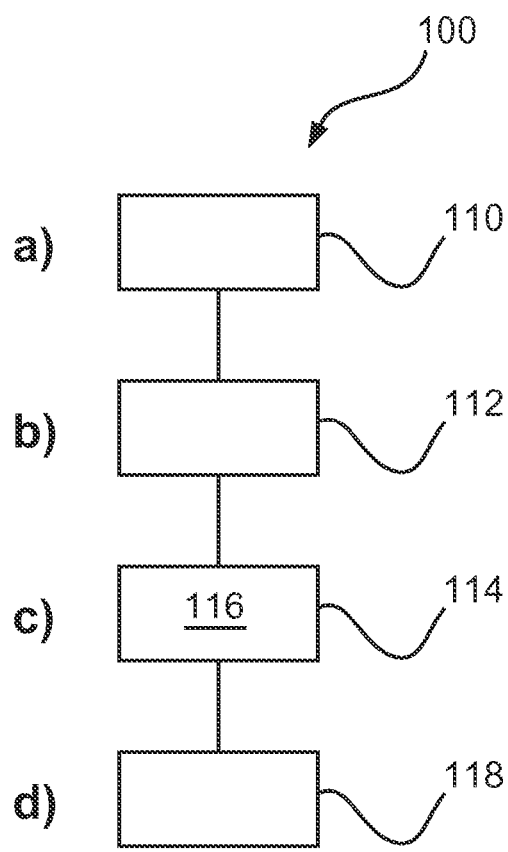
FIG. 3 shows basic steps of an example for a method for providing improved X-ray image navigation information.

FIG. 3 shows a method 100 for providing improved X-ray image navigation information, comprising the following steps: In a first step 110, an angiographic image of a region of interest of an object is provided. In a second step 112, a suppression area for partial bone suppression within the angiographic image is identified. In a third step 114, predetermined bone structures are identified and locally suppressed in the angiographic image in the suppression area, wherein a partly-bone-suppressed image 116 is generated. In a fourth step 118, the partly-bone-suppressed image 116 is displayed. The first step 110 is also referred to as step a), the second step 112 as step b), the third step 114 as step c), and the fourth step 118 as step d).

Figure 4:
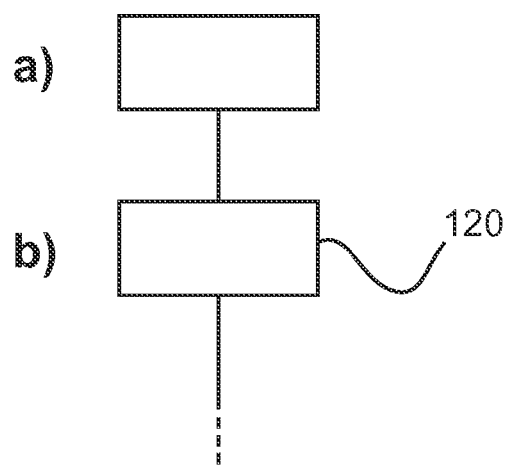
FIGS. 4 to 10 show further examples of methods for providing improved X-ray image navigation information.

According to the example shown in FIG. 4, step b) comprises identifying 120 of the suppression area by an input device.

Figure 5:
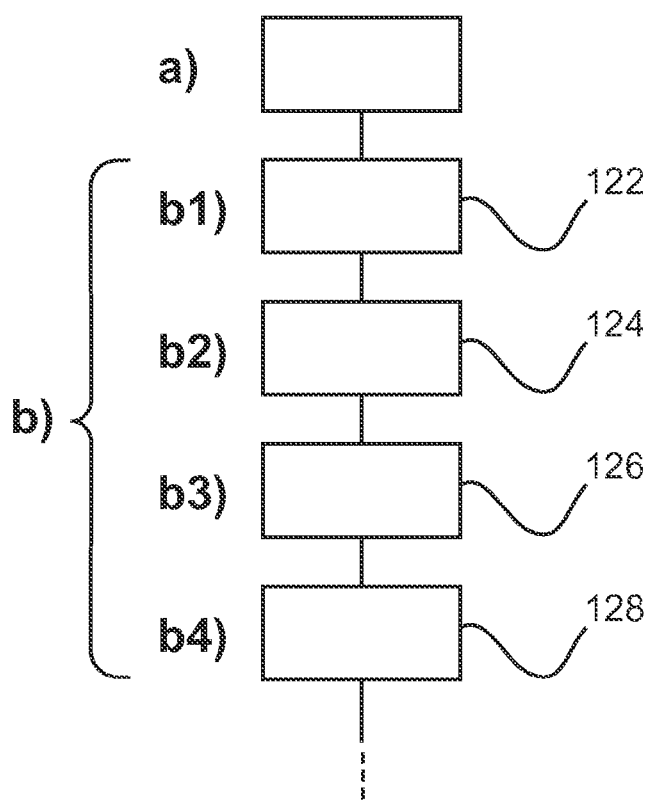

According to the example shown in FIG. 5, step b) comprises four sub-steps. In a first sub-step 122, a current fluoroscopy image of the region of interest is provided. In a second sub-step 124, a device is tracked in the fluoroscopy image. In a third sub-step 126, the fluoroscopy image and the angiographic image are registered. In a fourth sub-step 128, a position of the tracked device is registered to the angiographic image and a predefined region around the position of the device is defined as the suppression area. The first sub-step 122 is also referred to as step b1), the second sub-step 124 as step b2), the third sub-step 126 as step b3), and the fourth sub-step 128 as step b4).

A device mask may be created in step b2).

Figure 6:
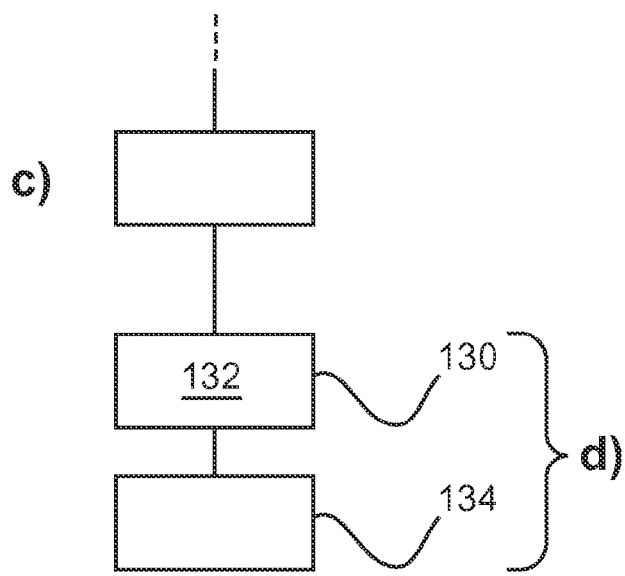

According to the example shown in FIG. 6, in step d), the partly-bone-suppressed image is combined in a first further sub-step 130 with image data from the fluoroscopy image forming a partly-bone-suppressed roadmap 132. In a second further sub-step 134, the partly-bone-suppressed roadmap 132 is displayed.

Figure 7:
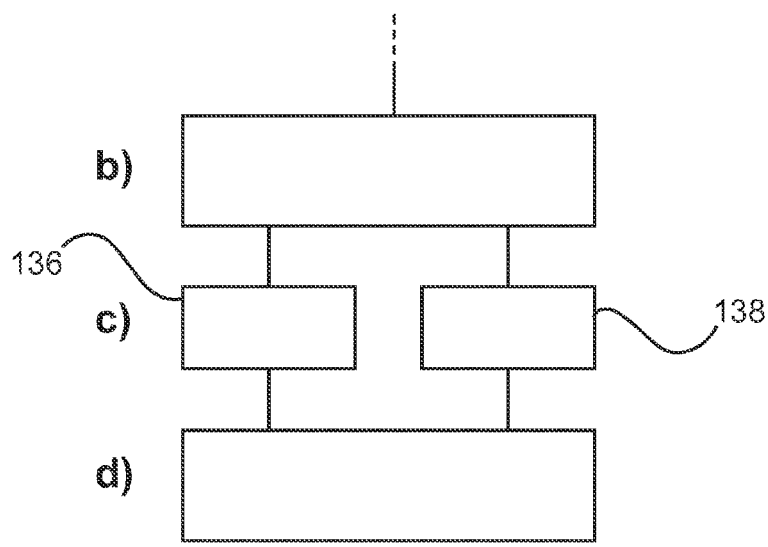

According to the example shown in FIG. 7, in step c), as a first option, a full suppression image is computed in step 136 for every detected bone, wherein the suppression is only visualized in the suppression area. As a second option, each bone structure intersecting with the suppression area is suppressed in step 138 along its complete detected length.

According to a further example, not shown, the bone structures outside the suppression area are maintained and kept visible as anatomical markers facilitating navigation.

Figure 8:
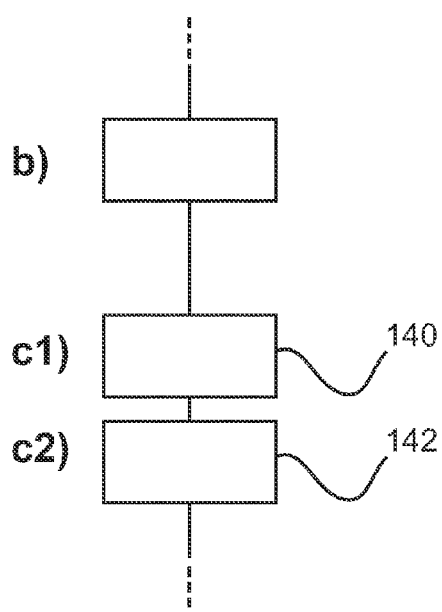

FIG. 8 shows a further example, according to which step c) comprises a first sub-step 140 of detecting and segmenting bone structures, and a second sub-step 142 of estimating their contribution to the X-ray projection. The first sub-step 140 is also referred to as step c1), and the second sub-step 142 is referred to as step c2).

Figure 9:
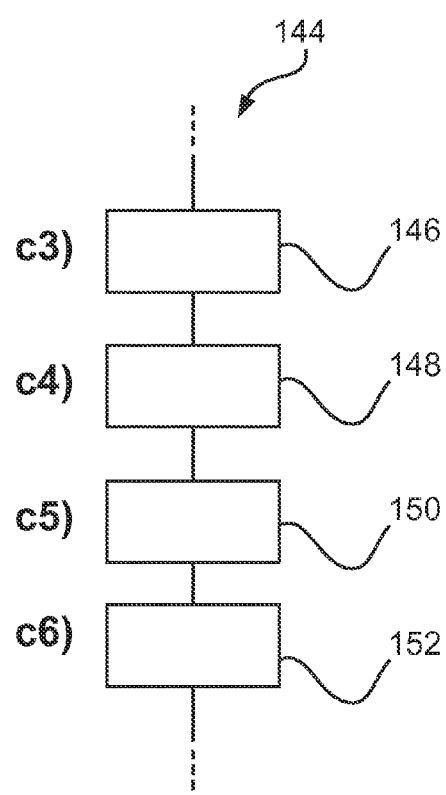

According to the example shown in FIG. 9, a sequence of angiographic images and a sequence of fluoroscopy images are provided, as indicated with arrow 144. Further, step c) comprises four sub-steps. In a first sub-step 146, the detected bone structures are registered on each angiogram image. In a second sub-step 148, it is determined to which of the angiograms the current fluoroscopy image corresponds. In a third sub-step 150, motion between the determined angiogram and the current fluoroscopy image is estimated. Still further, in a fourth sub-step 152, an intersection between the registered bone structures and the registered suppression area is computed and a region of interest, in which the bones are to be suppressed, is outputted. The first sub-step 146 is also referred to as step c3), the second sub-step 148 as step c4), the third sub-step 150 as step c5), and the fourth sub-step 152 as step c6).

Figure 10:
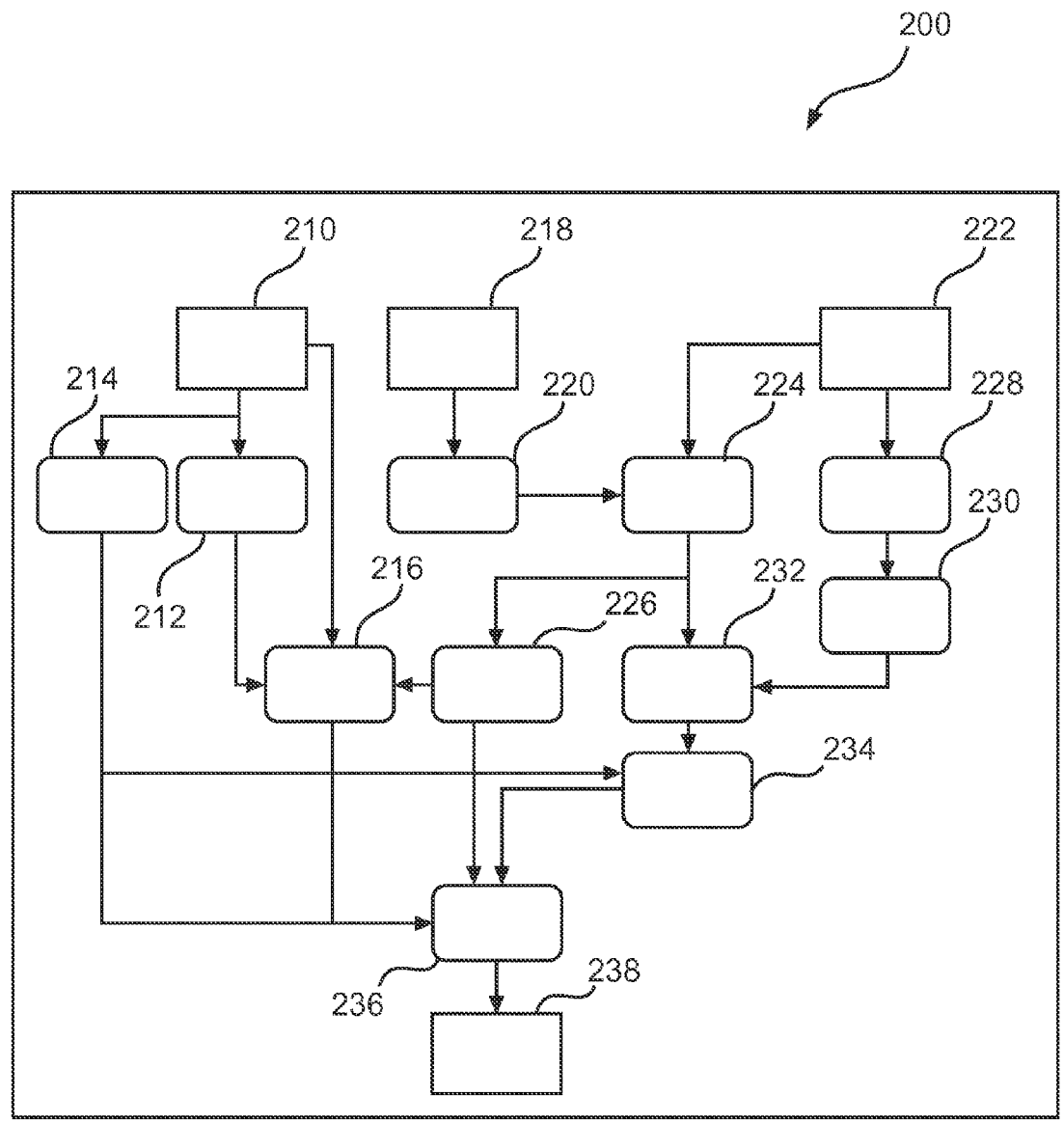

For example, the region of interest is the heart, and the method provides navigation support in cardiac procedures FIG. 10 shows a further example of the method, which shall be explained in the following. FIG. 10 shows a method 200, in which angiographic images are provided before injection; this is indicated with a first frame 210. As a first following step 212, bone structures are detected and a second step 214 is provided for estimating the bone structure's contribution. Next, a step 216 is provided, in which the detected bone structures are registered on each injected frames of an angiogram to be displayed. A further frame 218 indicates the provision of angiogram images after injection; these are provided to a step 220 of cardiac cycle extraction. A further frame 222 indicates the provision of fluoroscopy images. In a further step 224, the angiograms provided in step 218 and the fluoroscopy images of step 222 are used for a fluoro-angio-motion estimation, for which it is determined to which of the angiogram images the current fluoroscopy image corresponds, and the motion between these two frames is estimated. The result is then used in a further step 226 of an angio-image selection. The fluoroscopy images provided in frame 222 are also used for a device detection 228, which then leads to a device mask computing step 230, which device mask is used in a registration step 232, in which the result from the estimation step 224 is used for a device mask registration together with the device masks from step 230. In the device mask registration 232, the device mask is corrected with the estimated motion. In a further step 234, the intersection between the registered bone structures from step 214 is used to compute the intersection between the registered bone structures and the registered device mask, and to output a region of interest in which the bones would have to be suppressed. In further step 236, also referred as bone suppression step, the bones that intersect with the region of interest, as provided by the result of step 214 together with the result of the suppression region of interest computing, are suppressed. The subtraction may be visualized using a smooth feathering/blending for both suppression borders as well as progression of the suppression. Further, a step 238 of outputting an angio-image showing the result is provided.

Frames with rectangular corners indicate the provision of input and output image data, and frames with rounded corners indicate image processing steps.

In another example, the degree of suppression can be controlled, for example between minimum, e.g. 1, 2, or 5%, up to 100%, i.e. removing only a certain fraction of the contrast caused by the bones. In another example, the degree of suppression can depend on both the extent, i.e. the size of the structure to be suppressed (boundary), as well as the distance to the navigation instrument, so that parts of a bone distant to the instrument will remain.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical image viewing device for navigation in X-ray imaging, comprising:
a processor configured to receive an angiographic image of a region of interest of an object, to identify a suppression area for partial bone suppression within the angiographic image, and to identify and locally suppress bone structures in the angiographic image in the suppression area of the region of interest, while providing bone structures outside the suppression area, yet in the region of interest, to generate a partly-bone-suppressed image; and
a display configured to display the partly-bone-suppressed image.

2. The medical image viewing device according to claim 1,
wherein the processor is further configured to receive a current fluoroscopy image of the region of interest from an image acquisition device; to track a device in the current fluoroscopy image; to register the current fluoroscopy image and the angiographic image; to transfer a position of the tracked device to the angiographic image and to define a predefined region around the position of the device as the suppression area.

3. The medical image viewing device according to claim 1, wherein the processor is further configured to receive a sequence of angiographic images and a sequence of fluoroscopy images from an image acquisition device; to register the identified bone structures in the suppression area on each angiogram image; to determine to which of the angiogram images a current fluoroscopy image corresponds; to estimate motion between the determined angiogram image and the current fluoroscopy image; and to compute an intersection between the registered bone structures and the identified suppression area and to output the region of interest including the suppression area in which the bone structures are to be suppressed.

4. A medical imaging system, comprising:
an X-ray image acquisition device comprising an X-ray source and an X-ray detector, and configured to provide X-ray images of an object; and
the medical image viewing device according to claim 1, wherein the angiographic image is received from the X-ray image acquisition device.

5. A method for providing improved X-ray image navigation information using a image processor, the method comprising steps:
a) receiving an angiographic image of a region of interest of an object;
b) identifying a suppression area in the region of interest for partial bone suppression within the angiographic image based, at least in part, on the angiographic image and at least one fluoroscopic image provided by an X-ray image acquisition device;
c) identifying and locally suppressing bone structures in the angiographic image in the suppression area, while maintaining the bone structures outside the suppression area, yet in the region of interest, to generate a partly-bone-suppressed image; and
d) providing the partly-bone-suppressed image to a display for displaying the partly-bone-suppressed image.

6. The method according to claim 5, wherein step b) comprises identifying the suppression area by an input device.

7. The method according to claim 5, wherein step b) comprises:
b1) providing a current fluoroscopy image of the region of interest;
b2) tracking a device in the current fluoroscopy image;
b3) registering the fluoroscopy image and the angiographic image; and
b4) transferring a position of the tracked device to the angiographic image and defining a predefined region around the position of the device as the suppression area.

8. The method according to claim 7, further comprising combining the partly-bone-suppressed image with image data from the current fluoroscopy image to form a partly-bone-suppressed roadmap; wherein the partly-bone-suppressed roadmap is displayed.

9. The method according to claim 7, further comprising receiving a sequence of angiographic images; and receiving a sequence of fluoroscopy images; and wherein step c) comprises sub-steps:
c3) registering the identified bone structures on each angiogram image;
c4) determining to which of the angiograms the current fluoroscopy image corresponds;
c5) estimating motion between the determined angiogram and the current fluoroscopy image; and
c6) computing an intersection between the registered bone structures and the identified suppression area and outputting the region of interest including the suppression area in which the bone structures are to be suppressed.

10. The method according to claim 5, wherein in step c) comprises:
i) computing a full suppression image for every detected bone, wherein the suppression is only visualized in the suppression area; or
ii) suppressing each bone structure intersecting with the suppression area along its complete detected length.

11. The method according to claim 5, wherein bone structures outside the suppression area are kept visible as anatomical markers facilitating navigation.

12. The method according to claim 5, wherein step c) comprises sub-steps:
c1) detecting and segmenting bone structures; and
c2) estimating respective contributions of the segmented bond structures to the at least one fluoroscopic image.

13. The method according to claim 5, wherein the region of interest is a heart; and wherein the method provides navigation support in cardiac procedures.

14. A non-transitory computer readable medium storing a program, executable by a computer processor, for providing X-ray image navigation information using a image processor, the computer readable medium comprising:
receiving code for receiving an angiographic image of a region of interest of an object;
identifying code for identifying a suppression area in the region of interest for partial bone suppression within the angiographic image based, at least in part, on the angiographic image and at least one fluoroscopic image provided by an X-ray image acquisition device;
suppressing code for identifying and locally suppressing bone structures in the angiographic image in the suppression area, while maintaining the bone structures outside the suppression area, yet in the region of interest, to generate a partly-bone-suppressed image; and
display code for causing the partly-bone-suppressed image to be displayed.

* * * * *